United States Patent [19]

Campbell

[11] Patent Number: 4,665,920
[45] Date of Patent: May 19, 1987

[54] SKELETAL TISSUE STIMULATOR AND A LOW VOLTAGE OSCILLATOR CIRCUIT FOR USE THEREIN

[75] Inventor: Wayne A. Campbell, London, Canada

[73] Assignee: Minnesota Mining and Manufacturing Company, St. Paul, Minn.

[21] Appl. No.: 675,725

[22] Filed: Nov. 28, 1984

[51] Int. Cl.$^4$ .............................................. A61N 1/36
[52] U.S. Cl. ................................... 128/422; 128/419 F
[58] Field of Search ..................... 128/419 F, 421–422, 128/241; 331/111, 113 R, 423 R

[56] References Cited

U.S. PATENT DOCUMENTS

| | | | |
|---|---|---|---|
| 3,311,111 | 3/1967 | Bowers | 128/422 |
| 3,348,167 | 10/1967 | Gauld | 331/111 |
| 3,508,167 | 4/1970 | Russell, Jr. | 128/422 |
| 3,807,410 | 4/1974 | Wall et al. | 128/422 |
| 3,807,411 | 4/1974 | Harris et al. | 128/422 |
| 4,001,723 | 1/1977 | Sheng et al. | 331/111 |
| 4,168,711 | 9/1979 | Cannon, III et al. | 128/419 D |
| 4,333,469 | 6/1982 | Jeffcoat et al. | 128/419 F |

OTHER PUBLICATIONS

J. Watson, Light-Weight Battery Operable Orthopaedic Stimulator for the Treatment of Long-Bone Nonunions Using Pusled Magnetic Fields—Med. & Biol. Eng & Comput., 1983, 21, 509–510.

*Primary Examiner*—William E. Kamm
*Attorney, Agent, or Firm*—Donald M. Sell; James A. Smith; William D. Bauer

[57] ABSTRACT

A skeletal tissue stimulator and especially a bone growth stimulator 10 and a circuit 12 adapted to be coupled to the skeletal tissue in a body, and especially bone tissue in the body, whose growth is to be stimulated, which tissue acts as a load 22 for the circuit 12. The circuit 12 has a battery 24 and an oscillator circuit 26 which is adapted to be coupled to the load 22. The oscillator circuit 26 is coupled to a storage device 28 which is charged from the battery 24 and discharged through the load 22. The storage device 28 controls the state of the oscillator circuit 26 which in turn controls current flow from the battery 24 directly through load 22. The bone growth stimulator 10 and circuit 12 are characterized in that all the current provided by the battery 24 must flow through the load 22, either directly from the oscillator circuit 26 or as a result of discharge from the storage device 28.

3 Claims, 5 Drawing Figures

SKELETAL TISSUE STIMULATOR AND A LOW VOLTAGE OSCILLATOR CIRCUIT FOR USE THEREIN

BACKGROUND OF THE INVENTION

The present invention relates to skeletal tissue stimulators, more particularly bone growth stimulators and still more particularly to low voltage oscillator circuits for use in such stimulators.

It is known that, in certain circumstances, the application of an electrical current to skeletal tissue, especially bone tissue, may promote growth of that skeletal tissue. This is particularly useful in situations of non-union or delayed union of fractures of bones.

In one type of a typical skeletal tissue stimulator, a pair of electrodes are invasively inserted near the fracture site. These electrodes are then connected to an electrical circuit which passes electrical current between the electrodes and, hence, to the bone tissue. The electrical circuit determines the amount of and the characteristics of the electrical current which is passed to the electrodes and which is then utilized to stimulate the skeletal tissue.

A variety of electrical current wave forms have been used for skeletal tissue, especially bone, stimulation. In the past, electrical currents involving direct current wave forms and alternating current wave forms have been used. Alternating current wave forms with differing amplitudes, frequencies, duty cycles and average DC levels have been utilized. One example of an electrical current which has been found to be useful in skeletal tissue stimulators is an electrical pulsed current wave form of approximately 20 microamperes with approximately 50% duty cycle. In this electrical current wave form, an approximate DC current is applied for approximately one half of the time and a low electrical current is applied for remaining approximately one half time. Such an electrical current wave form then resembles an approximate square wave with a DC shift of approximately one half of the peak-to-peak value.

In certain skeletal tissue, e.g. bone, stimulators, it is desired to implant the entire stimulation unit in order to avoid a percutaneous connection between the electrodes and the stimulation unit. In this situation, several countervailing practical constraints tend to limit the usefulness of the stimulation device.

First, since the device is implanted or otherwise located near the site of stimulation, there is a need to have a compact unit. The compactness of the stimulation device necessarily limits its size and, hence, the capacity of its energy source, i.e. battery.

Second, since the effectiveness of the stimulation is, to a certain extent, the result of the magnitude of the electrical current induced into the skeletal tissue, the circuit must be capable of supplying and maintaining an electrical current at that level. This requirement militates toward a larger energy source, i.e. battery.

Third, since the device is invasive, i.e. implanted near the skeletal tissue to be stimulated, it is desirable to extend the lifetime of the energy source, i.e. battery, in order to achieve a maximum amount of stimulation with a minimum amount of use of invasive procedures.

SUMMARY OF THE INVENTION

The present invention provides an implantable low voltage oscillator circuit which is capable of being coupled to a portion of the body which acts as a load to the circuit. The circuit has a battery with a first terminal and a second terminal. The circuit also has an oscillator having a first state and a second state and being operatively coupled to the first terminal of the battery. The circuit also has a capacitive storage means operatively coupled between the oscillator and the second terminal of the battery for controlling the oscillation of the oscillator. The circuit also has a charging device operatively coupled to the capacitive storage means for charging the capacitive storage means when the oscillator is in the first state. The circuit also has a discharge device operatively coupled between the capacitive storage means and the load for discharging the capacitive storage means through the load when the oscillator is in the second state. The capacitive storage means and the load are the only current paths to or from the second terminal of the battery.

The present invention also provides a skeletal tissue stimulator capable of being coupled to the skeletal tissue, e.g. bone, which acts as a load for the stimulator. A battery is utilized which has a first terminal and a second terminal. The second terminal of the battery is capable of being coupled to the skeletal tissue at a first location. A latch is operatively coupled to the first terminal of the battery and is capable of being coupled to the skeletal tissue at a second location. The latch has a first state and a second state. The latch allows electrical current to flow between the battery and the skeletal tissue when the latch is in the first state but does not allow electrical current to flow between the battery and the skeletal tissue when the latch is in the second state. A capacitor is operatively coupled between the latch and the second terminal of the battery. The capacitor controls the latch to the first state when the capacitor is substantially discharged and controls the latched to the second state when the capacitor is substantially charged. A charger is operatiavely coupled to the battery and the capacitor for charging the capacitor from the battery when the latch is in the first state. A discharger is operatively coupled to the capacitor and is capable of being coupled to the skeletal tissue and allows the capacitor to discharge through the skeletal tissue when the latch is in the second state.

The present invention also provides a skeletal tissue stimulator, e.g. a bone growth stimulator, which is adapted to be coupled to a load, a portion of which is adapted to be the skeletal tissue in a body whose growth is to be stimulated. The skeletal tissue stimulator has a battery and an oscillator circuit coupled to the battery and adapted to be coupled to the load. An oscillator circuit has a first state in which current is allowed to flow between the battery and the load and a second state in which current is not allowed to flow between the battery and the load. The oscillator circuit has a storage element adapted to be ranged in parallel with the load, the storage element being charged from the battery and being adapted to be discharged through the load. The stimulator is characterized in that all current provided by the battery must flow through either the storage element or the load.

A skeletal tissue stimulation device or a low voltage oscillator for use in such a device characterized in this manner achieves several notable, significant advantages. First, the circuit operates from a low voltage energy source, i.e. a battery, which can be implanted near the stimulation site. Second, the circuit draws no, or very little electrical current from the energy source when there is no load (no tissue to be stimulated). This is significant so that a long shelf life can be achieved before the stimulation device is implanted and, hence, ready for stimulation. Third, while the circuit is in operation, all of the electrical current from the battery reaches the load, i.e., the skeletal tissue which is to be stimulated. This is because all of the current from the energy source either is allowed to flow directly to the skeletal tissue or to charge the capacitor, or capacitive storage means, which subsequently is discharged through the skeletal tissue. No other current, save for the leakage current of the capacitive device, flows from the battery or energy source. Fourth, the circuit provides a relatively stable electrical current output under a wide variety of load impedances. This result is significant because the impedance of the load, that is the impedance of the skeletal tissue which is to be stimulated, varies significantly from individual to individual and from implantation site to implantation site. Further, the circuit provides safe levels of electrical current under all possible load conditions.

BRIEF DESCRIPTION OF DRAWINGS

The foregoing advantages, construction and operation of the present invention will become more readily apparent from the following description and accompanying drawings in which.

DESCRIPTION OF THE PREFERRED EMBODIMENTS

Figure 1:
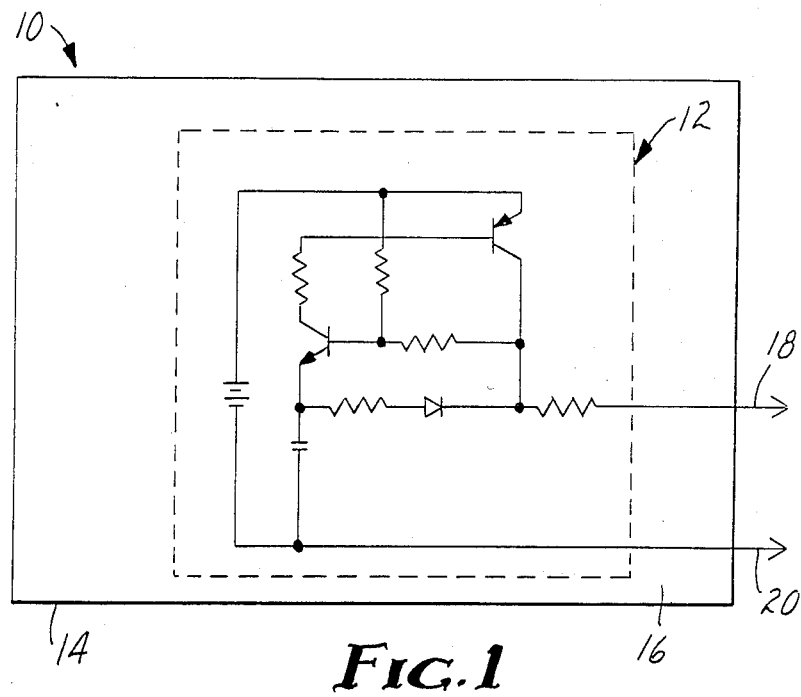
FIG. 1 is a diagram of a skeletal tissue stimulator of the present invention.

FIG. 1 discloses a skeletal tissue stimulator, e.g. a bone growth stimulator, 10 of the present invention. Skeletal tissue stimulator 10 contains circuit 12 contained within housing 14 secured with an appropriate potting material 16, such as Hysol epoxy. Output leads 18 and 20 from circuit 12 extend beyond housing 14. Skeletal tissue stimulator 10 may then be implanted into the body near the skeletal tissue, e.g. bone, which is to be stimulated. The skeletal tissue which is to be stimulated is located generally between output leads 18 and 20 which skeletal tissue forms the electrical load for circuit 12.

Figure 2:
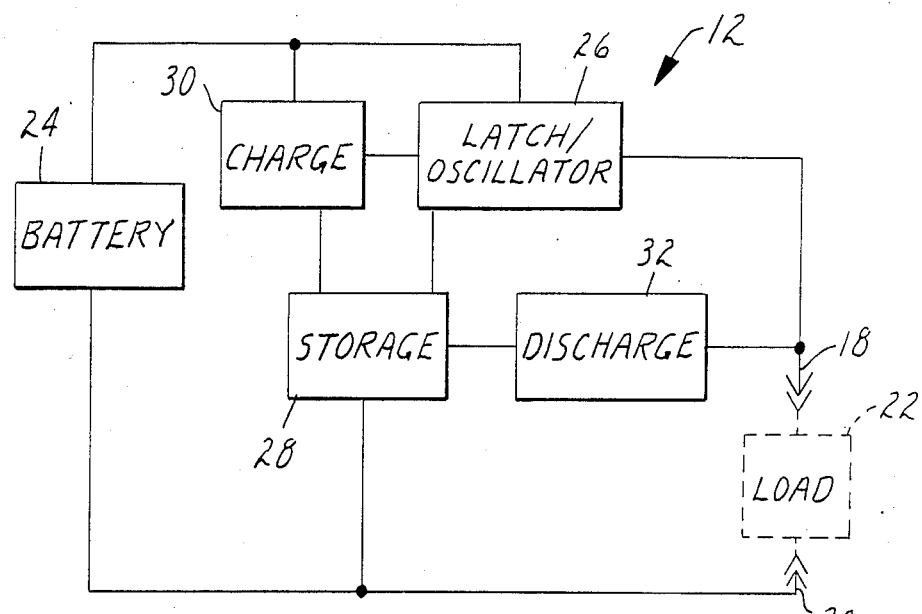
FIG. 2 is a block diagram of the circuit of the present invention.

FIG. 2 is a block diagram of the circuit 12 of the present invention. As in FIG. 1, circuit 12 has output leads 18 and 20 to which the skeletal tissue or load 22 may be connected. Circuit 12 consists of an energy source or a battery 24 which is coupled to an oscillator circuit 26. Oscillator circuit 26 is coupled to output lead 18 and to storage device 28. When oscillator circuit 26 is in one state, current from battery 24 may flow through oscillator 26 and subsequently load 22 by way of output leads 18 and 20 to provide a stimulating electric current to load 22. When oscillator 26 is in another state, very little or no electric current is allowed to flow through oscillator circuit 26 and, hence, through output leads 18 and 20 to load 22. Charging device 30 is coupled between battery 24 and storage device 28 for supplying charge to storage device 20 from battery 24 when storage device 28 is substantially discharged. Storage device 28 is coupled back to oscillator circuit 26, either through charging device 30 as shown in FIG. 2 or directly, in order for storage device 28 to change the state of oscillator circuit 26 depending upon the energy storage or charge state of storage device 28. Discharge device 32 is coupled between storage device 28 and output lead 18. Discharge device 32 provides a discharge path for storage device 28 through output leads 18 and 20 and, hence, through load 22.

Note in FIG. 2 that there are only 2 paths for electric current to flow to or from battery 24, i.e. through storage device 28 and through load 22. Also note that any energy stored in storage device 28 must be discharged through discharge device 32 through load 22. This arrangement provides a couple of unique advantages. First, an operation circuit 12 allows essentially all of the energy, i.e. electric current, from battery 24 to flow through load 22 and, hence, be useful in providing skeletal tissue stimulation. This results in an effective and efficient use of energy source or battery 24 and, hence, the longevity of circuit 12 when implanted and utilized. Second, that when load 22 is disconnected, i.e. when the circuit is not implanted with skeletal tissue to be stimulated, there is no path for electrical current to discharge battery 24. As previously discussed, the only two paths for electric current are through storage device 28 and through load 22. In addition, as previously discussed, storage device 28 must discharge through load 22 by way of discharge device 32. Thus, if load 22 is disconnected there is no path to discharge storage device 28 and, hence, there is no current flow to discharge battery 24. Of course, storage device 28 may not be a perfect storage device and, hence, may have a minute leakage current which for purposes of the present embodiment is negligible and can be ignored.

Figure 3:
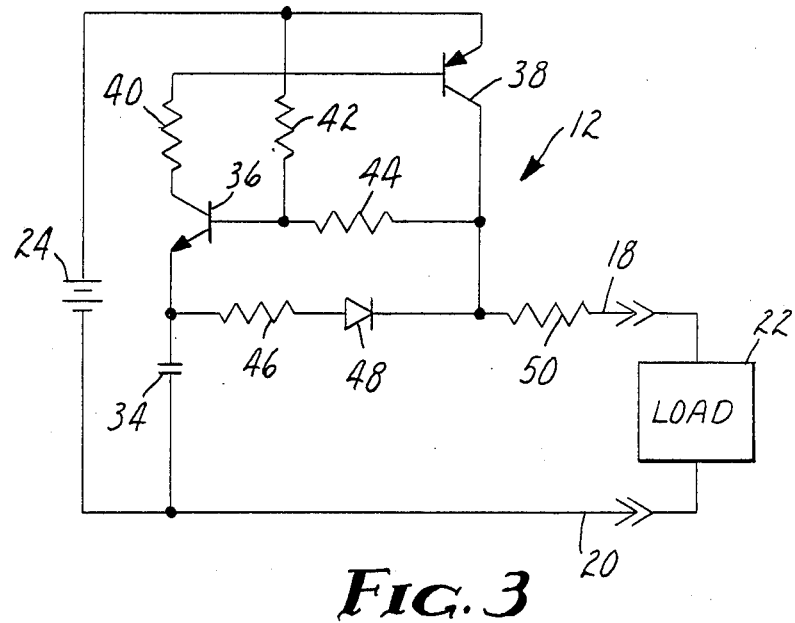
FIG. 3 is a detailed circuit diagram of a preferred embodiment of the present invention.

A more detailed understanding of the operation of circuit 12 may be had by reference to the detailed circuit diagram of a preferred embodiment of the present invention as illustrated in FIG. 3. As in FIG. 2, load 22 is coupled to circuit 12 with output leads 18 and 20. Circuit 12 also contains a battery 24. Storage device 28 is represented by capacitor 34. Transistors 36 and 38 along with resistors 40, 42 and 44 form oscillator circuit 26 and charging device 30. Resistor 46 and diode 48 form discharge device 32. Resistor 50 is coupled between diode 48 and transistor 38 and output lead 18.

Figure 4:
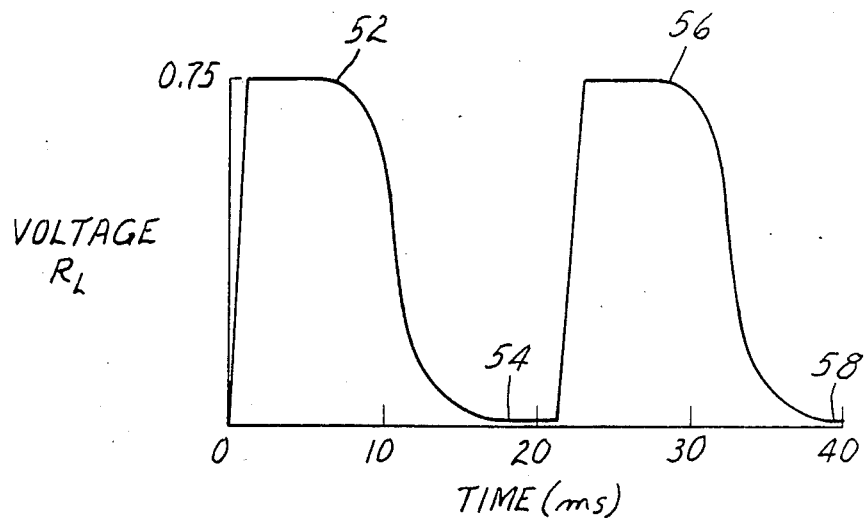
FIG. 4 is an electrical voltage wave form of the output of the circuit of the present invention taken across the load.

Operation of the detailed circuit diagram of FIG. 3 is as follows. When capacitor 34 is in its discharged state, transistor 36 will be on which in turn will turn on transistor 38. The collector of transistor 38 will go high and result in current flow through resistor 50, output leads 18 and 20 through load 22. As this occurs, the base current through transistor 36 will charge capacitor 34. As capacitor 34 becomes charged, the base voltage of transistor 36 will drop which will lower the collector current through transistor 36. This in turn will drop the base and collector voltages of transistor 38 and, hence, both transistors 36 and 38 will go off which will terminate current flow through transistor 38 to the load 22 resulting in no voltage on load 22. With transistors 36 and 38 off, capacitor 34 will discharge through resistor 46, diode 48 and resistor 50 through load 22. As capacitor 34 is discharged, the cycle then repeats itself. This results in the voltage wave form 52 illustrated in FIG. 4. As transistors 36 and 38 turn on, current is allowed to flow through transistor 38 and, hence, through resistor 50 to load 22. For the voltages and components preferred in FIG. 3, this results in a 0.75 volt potential across an exemplary resistive load of 47 kilohms which is exemplary of a skeletal tissue load. As capacitor 34 becomes charged and, hence, transistors 36 and 38 turn off, capacitor 34 then discharges through load 22. This is represented at point 54 on the wave form in which the electric current through the load is formed by the discharge from capacitor 34 and results in a voltage of approximately 0.3 volts across resistive load 22. The wave form repeats itself at points 56 and 58 corresponding to previously described points 52 and 54.

The circuit of the present invention and, hence, the skeletal tissue stimulator of the present invention involve several distinguished, advantageous characteristics. When there is no resistive load 22, capacitor 34 cannot discharge and, hence, battery 24 cannot be drained. This will enhance and prolong the shelf life of the skeletal tissue stimulator prior to its implantation and use as a skeletal tissue stimulator. Second, all of the electrical current involved in charging capacitor 34 subsequently passes through load 22 when capacitor 34 discharges. This results in the efficient use of the energy stored in battery 24 and results in essentially all of the electric current from battery 24 resulting in skeletal tissue stimulation through load 22. With the inclusion of resistor 50, half of the voltage from the output of the circuit 12 will be dropped across resistor 50 since resistor 50 is approximately equal the expected resistive component of load 22. However, the loss of half of the voltage is appropriate since it is much more important in a skeletal tissue stimulator to maintain the proper electric current level. The use of resistor 50 stabilizes the output electric current over a wider range of resistive loads.

Figure 5:
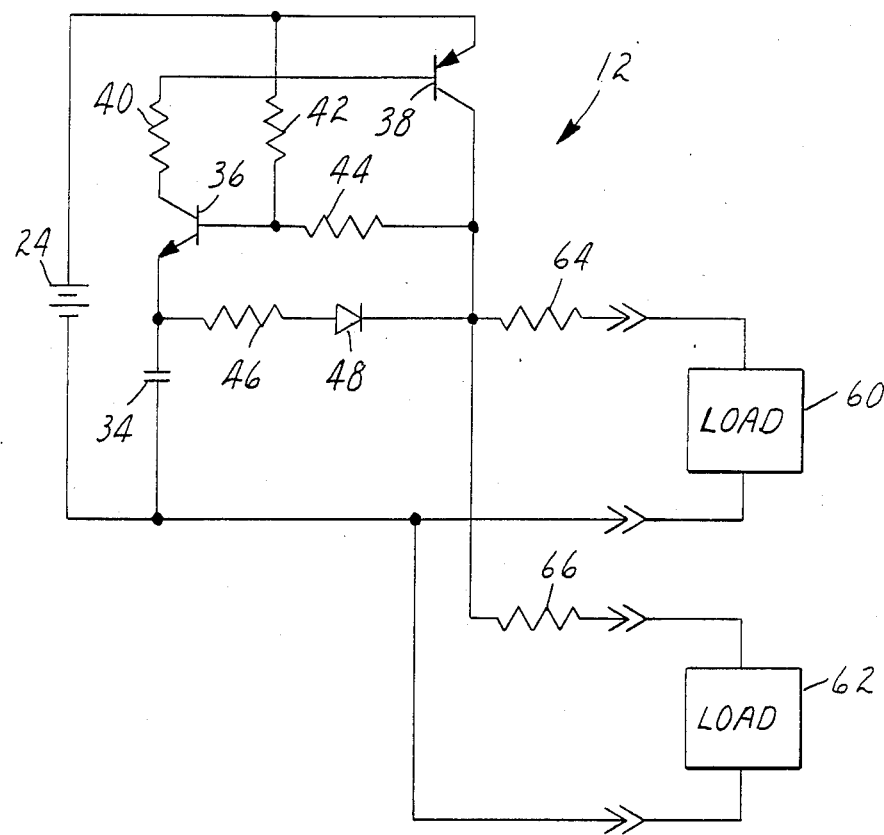
FIG. 5 is a detailed circuit diagram of an alternative embodiment of the present invention.

FIG. 5 represents an alternative skeletal tissue stimulator utilizing an electric circuit 12 in which the output current from the circuit 12 could drive two loads 60 and 62. In this case, one skeletal tissue stimulator circuit 12 could drive two pairs of electrodes and stimulate skeletal tissue in two different locations. The loads 60 and 62 are essentially coupled in parallel with each other at the output of transistor 38. Buffering resistance 50 as in FIG. 3 may be split into resistances 64 and 66 as illustrated in FIG. 5 or they may be combined in one resistance and the loads split following the passage through this resistance.

Thus, it can be seen that there has been shown and described a novel skeletal tissue stimulator and a novel circuit for use in a skeletal tissue stimulator. It is to be recognized and understood, however, that various changes, substitutions and modifications in the details of the described invention can be made by those of skill in the art without departing from the scope of the invention as defined in the following claims.

I claim:

1. An implantable low voltage oscillator circuit, capable of being coupled to a portion of the body which body acts as a load to said circuit, comprising:

a battery having a first terminal and a second terminal;

an oscillator having a first state and a second state and being operatively coupled to said first terminal of said battery;

capacitive storage means operatively coupled between said oscillator and said second terminal of said battery for controlling the oscillation of said oscillator;

charge means operatively coupled to said capacitive storage means, said charge means for charging said capacitive storage means when said oscillator is in said first state; and discharge means operatively coupled to said capacitive storage means and capable of being coupled to said load, said discharge means for discharging said capacitive storage means through said load when said oscillator means is in said second state;

said capacitive storage means and said load being the only current paths to or from said second terminal of said battery.

2. A skeletal tissue stimulator capable of being coupled to said skeletal tissue which acts as a load for said stimulator, comprising:

a battery having a first terminal and a second terminal, said second terminal capable of being coupled to said skeletal tissue at a first location;

a latch operatively coupled to said first terminal of said battery and capable of being coupled to said skeletal tissue at a second location, said latch having a first state and a second state, said latch for allowing electrical current to flow between said battery and said skeletal tissue when said latch is in said first state but not allowing electrical current to flow between said battery and said skeletal tissue when said latch is in said second state;

a capacitor operatively coupled between said latch and said second terminal of said battery, said capacitor for controlling said latch to said first state when said capacitor is substantially discharged and for controlling said latch to said second state when said capacitor is substantially charged;

charging means operatively coupled to said battery and said capacitor for charging said capacitor from said battery when said latch is in said first state; and discharge means operatively coupled to said capacitor and capable of being coupled to said skeletal tissue for allowing said capacitor to discharge through said skeletal tissue when said latch is in said second state.

3. A skeletal tissue stimulator adapted to be coupled to a load, a portion of which is adapted to be said skeletal tissue, comprising:

a battery; and an oscillator circuit coupled to said battery and adapted to be coupled to said load;

said oscillator circuit having a first state in which current is allowed to flow between said battery and said load and having a second state in which current is not allowed to flow between said battery and said load;

said oscillator circuit having a storage element adapted to be arranged in parallel with said load, said storage element being charged from said battery and being adapted to be discharged through said load;

said stimulator characterized in that all current provided by said battery must flow through either said storage element or said load.

* * * * *